US00PP20077P2

(12) United States Plant Patent
Ackerman et al.

(10) Patent No.: US PP20,077 P2
(45) Date of Patent: Jun. 9, 2009

(54) STRAWBERRY PLANT NAMED 'PRESTIGE'

(50) Latin Name: *Fragaria ananassa*
Varietal Denomination: PRESTIGE

(75) Inventors: Stephen M. Ackerman, Salinas, CA (US); Steven D. Nelson, Watsonville, CA (US); Michael D. Nelson, Watsonville, CA (US)

(73) Assignees: Plant Sciences, Inc., Watsonville, CA (US); Berry R&D, Inc., Watsonville, CA (US)

( * ) Notice: Subject to any disclaimer, the term of this patent is extended or adjusted under 35 U.S.C. 154(b) by 0 days.

(21) Appl. No.: 12/150,520

(22) Filed: Apr. 29, 2008

Related U.S. Application Data

(60) Provisional application No. 60/996,102, filed on Nov. 1, 2007.

(51) Int. Cl.
*A01H 5/00* (2006.01)

(52) U.S. Cl. ..... Plt./209

(58) Field of Classification Search ..... Plt./209
See application file for complete search history.

*Primary Examiner*—Annette H Para
(74) *Attorney, Agent, or Firm*—Foley & Lardner LLP

(57) ABSTRACT

This invention relates to a new and distinct variety of strawberry plant named 'PRESTIGE'. This new strawberry plant named 'PRESTIGE' is primarily adapted to the growing conditions of the central coast of California, and is primarily characterized by its medium to large plant size; medium fruit size; spreading calyx segments; long petiolule length; three to four leaflets/tri-foliate; moderate fruit production with very good flavor; and medium green foliage with medium glossy texture and medium interveinal blistering.

5 Drawing Sheets

Latin name of the genus and species of the plant claimed: *Fragaria ananassa.*
Variety denomination: 'PRESTIGE'.

BACKGROUND OF THE INVENTION

The present invention relates to a new and distinct strawberry variety named 'PRESTIGE'. This new variety is a result of a controlled cross made in 2000 in an ongoing breeding program between strawberry variety designated 'PS-1269' (patented, U.S. Plant Pat. No. 10,686) and strawberry variety designated 'PS-3523' (patented, U.S. Plant Pat. No. 14,447). The variety is botanically known as *Fragaria ananassa.*

The seedling resulting from the aforementioned cross was selected from a controlled breeding plot in Monterey County, California in the summer of 2002. After its selection, the new variety was asexually propagated by stolons in both San Joaquin County, California and Siskiyou County, California. The new variety was extensively tested over the next several years in fruiting fields in Monterey County, California. This propagation has demonstrated that the combination of traits disclosed herein as characterizing the new variety are fixed and remain true to type through successive generations of asexual reproduction.

BRIEF SUMMARY OF THE INVENTION

'PRESTIGE' is primarily adapted to the climate and growing conditions of the central coast of California. The nearby Pacific Ocean provides the needed humidity and moderate temperatures to produce a strong vigorous plant and maintain fruit quality during the spring, summer and fall production months.

The following traits have been repeatedly observed and are determined to be unique characteristics of 'PRESTIGE', which in combination distinguish this strawberry plant as a new and distinct variety:

1. Medium to large plant size;
2. Medium fruit size;
3. Spreading calyx segments;
4. Long petiolule length;
5. Three to four leaflets/tri-foliate;
6. Moderate fruit production with very good flavor; and
7. Medium green foliage with medium glossy texture and medium interveinal blistering.

The strawberry varieties that are believed to be most closely related to the new strawberry variety 'PRESTIGE' are the strawberry variety 'PS-592' (patented, U.S. Plant Pat. No. 9,903) and the strawberry variety 'PS-4634' (patented, U.S. Plant Pat. No. PP 17,487). In comparison to the similar strawberry varieties 'PS-592' and 'PS-4634', the new strawberry variety 'PRESTIGE' differs by the following combination of characteristics as described in Table 1:

TABLE 1

| Characteristic | 'PRESTIGE' | 'PS-592' (U.S. Plant Pat. No. 9,903) | 'PS-4634' (U.S. Plant Pat. No. 17,487) |
|---|---|---|---|
| 1. Color of mature fruit | Red | Orange red to red | Red to orange red |
| 2. Average fruit weight (gm) | 23.8 | 24.3 | 26.8 |
| 3. Marketable yield (gm/plt) | 1,403 | 1,500 | 1,544 |
| 4. Attitude of the calyx | Spreading | Spreading to reflexed | Spreading to reflexed |
| 5. Time of first harvest | Medium | Early | Early |
| 6: Plant size | Medium to large | Large | Large |

TABLE 1-continued

| Characteristic | 'PRESTIGE' | 'PS-592' (U.S. Plant Pat. No. 9,903) | 'PS-4634' (U.S. Plant Pat. No. 17,487) |
|---|---|---|---|
| 7. Stolon diameter (mm) | 3.5 | 4.1 | 3.9 |
| 8. Interveinal leaf blistering | Medium | Medium to strong | Medium to strong |
| 9. Foliage gloss | Medium | Strong | Medium to strong |
| 10. Number of leaflets | Three to four | Three | Three |
| 11. Terminal leaf shape of base | Obtuse | Acute | Acute |
| 12. Petiolule length (mm) | 17.4 | 13.2 | 10.0 |

For identification a series of AFLP molecular markers have been determined for this new variety.

BRIEF DESCRIPTIONS OF THE PHOTOGRAPHS

The accompanying color photographs illustrate the overall appearance of typical specimens of the new strawberry variety 'PRESTIGE', at various stages of development as true as it is reasonably possible with color reproductions of this type. Color in the photographs may differ slightly from the color value cited in the botanical description which accurately describe the color of 'PRESTIGE'. The depicted plant and plant parts of the new strawberry variety 'PRESTIGE' were taken in Monterey County, California, and are approximately 8 to 9 months old:

DETAILED BOTANICAL DESCRIPTION

Figure 1:
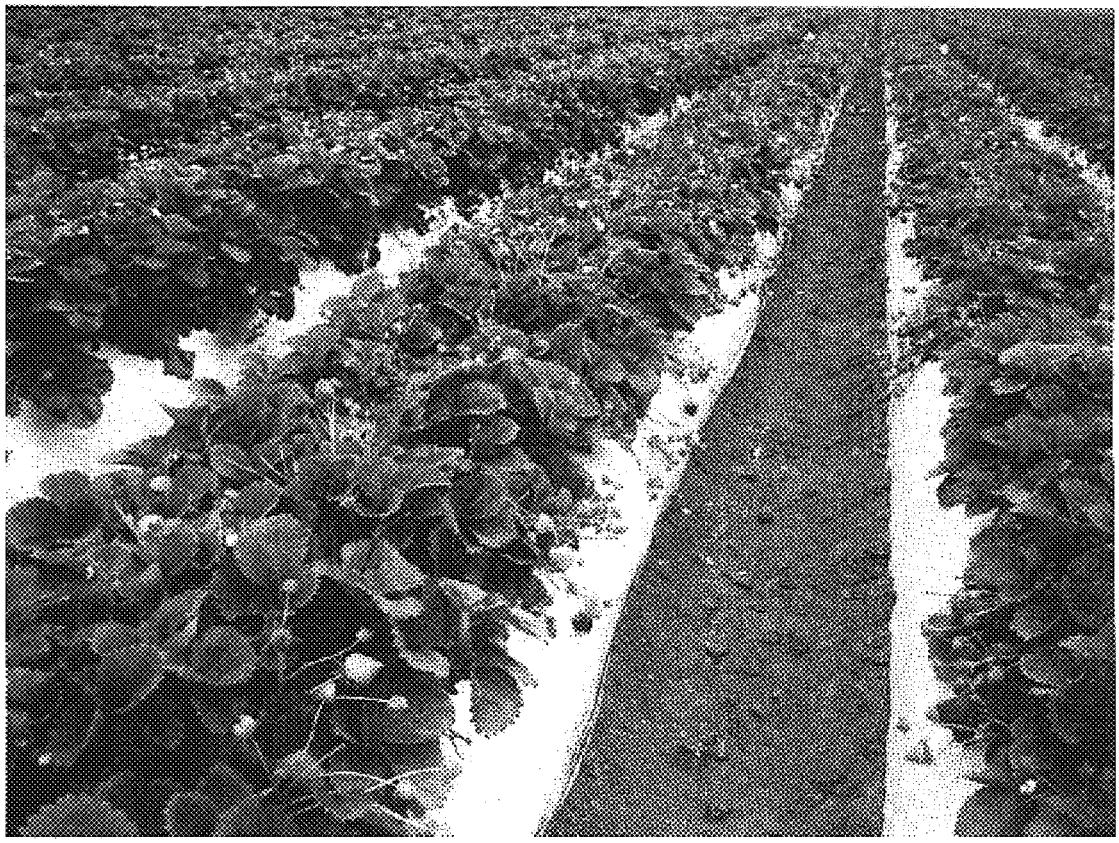
FIG. 1 shows typical fruiting field characteristics of 'PRESTIGE' taken in the month of July 2007.
Figure 2:
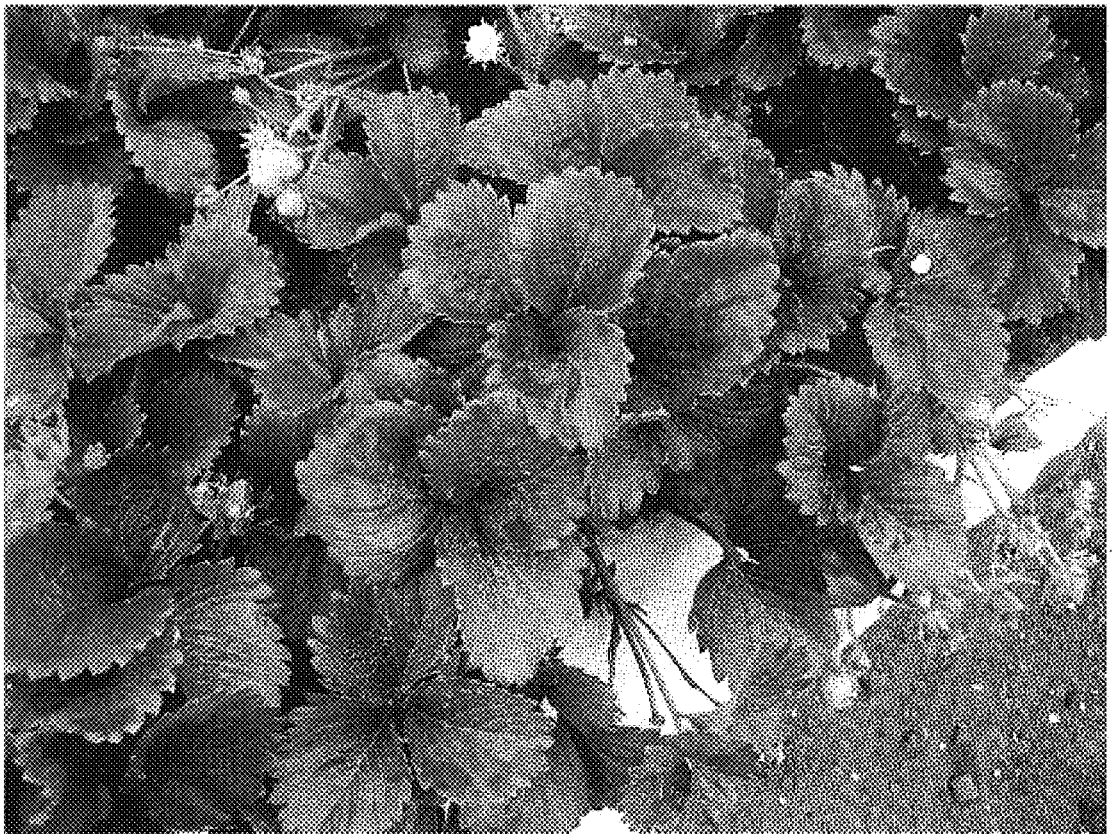
FIG. 2 shows a close-up view of a typical leaf structure of 'PRESTIGE' taken in the month of July 2007.
Figure 3:
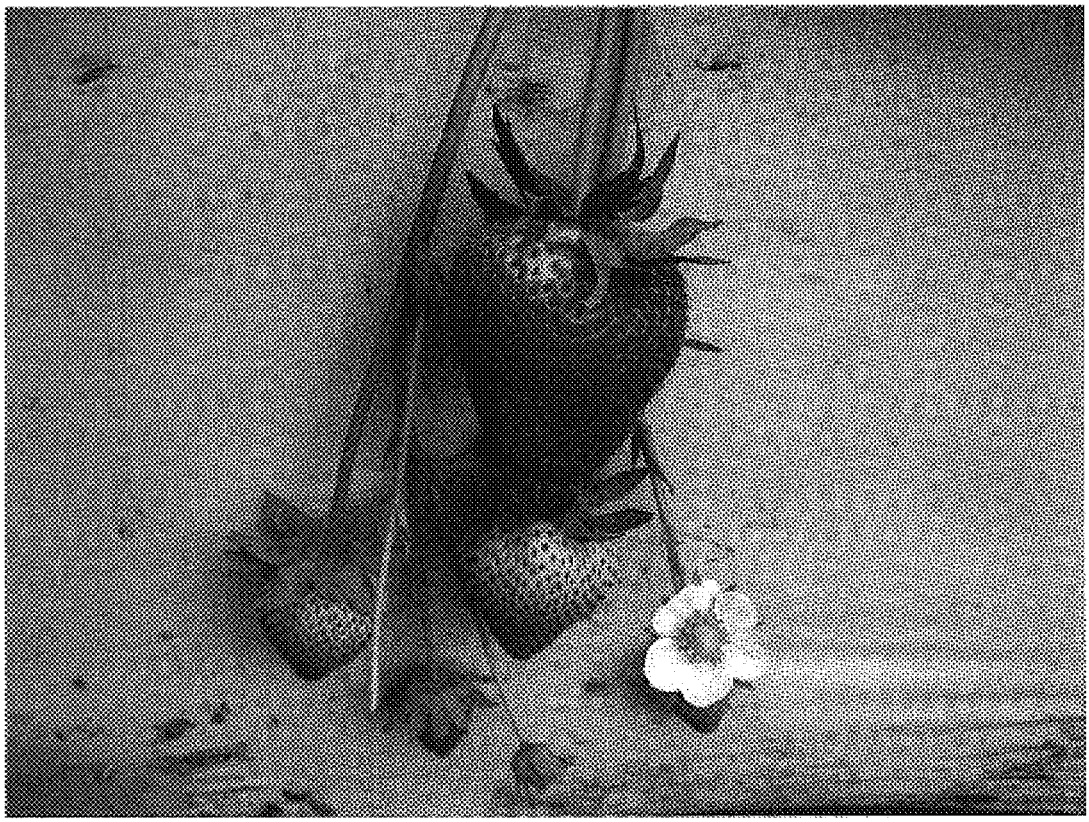
FIG. 3 shows typical mature and immature field fruit of 'PRESTIGE' taken in the month of July 2007.
Figure 4:
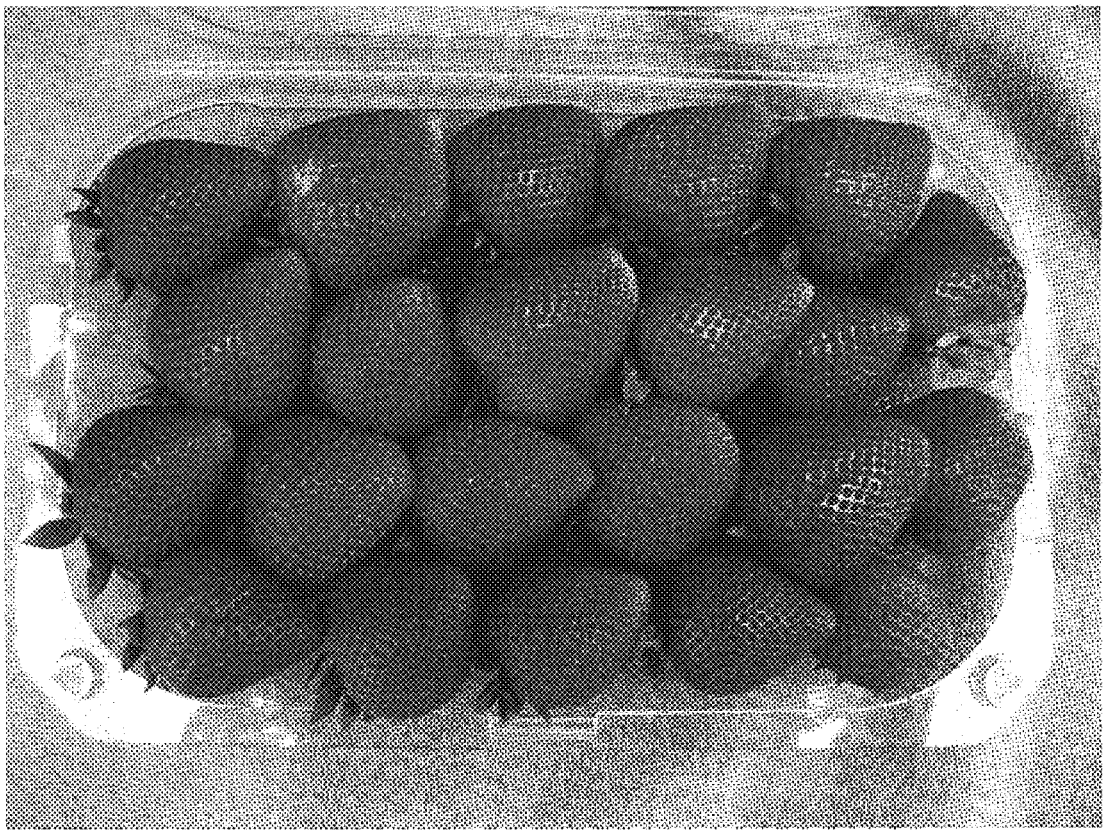
FIG. 4 shows a close-up view of mature fruit of 'PRESTIGE' taken in the month of July 2007.
Figure 5:
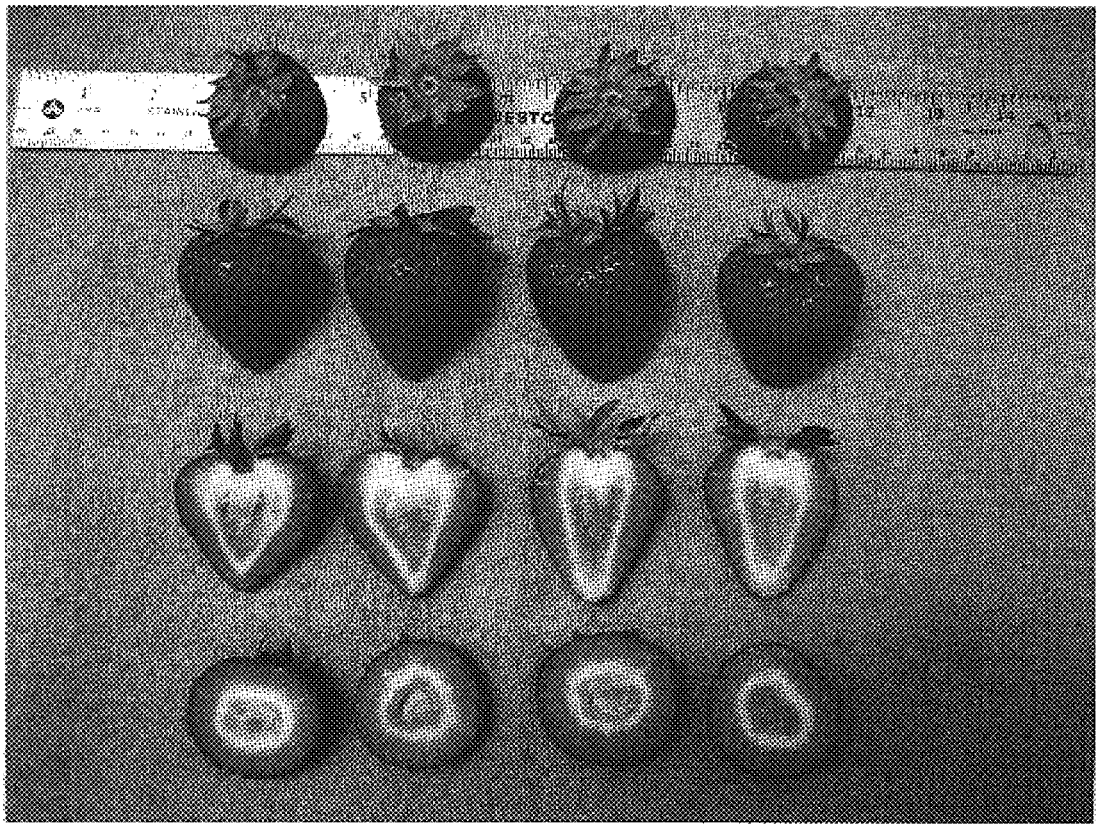
FIG. 5 shows typical internal and external mature fruit characteristics of 'PRESTIGE' taken in the month of July 2007.

'PRESTIGE' has not been observed under all possible environmental conditions. The characteristics of the new variety may vary in detail, depending upon variations in environmental factors, including weather (temperature, humidity and light intensity), day length, soil type and location.

The aforementioned photographs, together with the following description of the new variety 'PRESTIGE', unless otherwise noted, is based on observations taken during the 2007 growing season in Monterey County, California. These measurements and ratings were taken from plants of 'PRESTIGE' dug from a high-elevation nursery located in Siskiyou County, California during the middle of October 2006 and planted approximately 3 weeks later in Monterey County, California. The approximate age of the observed plants is 8 to 10 months. Yield observations and fruit quality characteristics are averaged from four years of data collected from the 2004 through 2007 growing seasons. Flower measurements and characteristics are from secondary flowers unless otherwise noted. Fruit characteristics and measurements are from secondary fruit unless otherwise noted.

Color terminology where noted follows the Munsell Book of Colors, Munsell Color, Baltimore Md. (1976).

The following Tables 8 describe fruit, plant, stolon, foliage, fruiting truss, flower and pest disease characteristics of the new strawberry 'PRESTIGE' in comparison to the similar strawberry variety 'PS-592' (patented, U.S. Plant Pat. No. PP 9,903) and strawberry variety 'PS-4634 ' (patented, U.S. Plant Pat. No. PP 17,487).

TABLE 2

FRUIT CHARACTERISTICS

| Characteristic | 'PRESTIGE' | 'PS-592' (U.S. Plant Pat. No. 9,903) | 'PS-4634' (U.S. Plant Pat. No. 17,487) |
|---|---|---|---|
| Color of mature fruit | 7.5R 3/10 to 4/10 Red | 7.5R 3/12 to 4/12 Orange red to red | 7.5R 3/12 to 4/12 Red to orange red |
| Color of internal flesh | 7.5R 4/10 to 4/12 Medium red | 7.5R 5/10 to 4/10 Light red | 7.5R 5/10 to 4/12 Medium to light red |
| Length (cm) | 4.6 | 4.7 | 4.8 |
| Width (cm) | 3.9 | 4.2 | 4.1 |
| Ratio length/width | 1.18 Slightly longer than broad | 1.13 Slightly longer than broad | 1.17 Slightly longer than broad |
| Calyx diameter (cm) | 4.5 | 4.7 | 4.3 |
| Average weight (gm) | 23.8 | 24.3 | 26.8 |
| Achene color | 5Y 5/6 to 7.5R 3/8 | 5Y 6/8 to 7.5R 3/8 | 5Y 6/8 to 7.5R 3/8 |
| Achenes per berry | 411 | 283 | 375 |
| Achene weight (mg) | 0.48 | 0.53 | 0.48 |
| Marketable yield (gm/plt) | 1,403 | 1,500 | 1,544 |
| Size | Medium | Medium to large | Large |
| Predominant shape | Conical | Conical | Conical |
| Difference in shapes between primary and secondary fruit | Slight | Slight to moderate | Moderate |
| Band without achenes | Absent or very narrow | Absent or very narrow | Narrow |
| Unevenness of surface | Absent or very weak | Absent or very weak | Weak to medium |
| Evenness of color | Even | Even | Slightly uneven to even |
| Glossiness | Medium to strong | Strong | Strong |
| Insertion of achenes | Level with surface | Level with surface | Level with surface |
| Insertion of calyx | Level with to in the basin | Level with to above the fruit | Level with to above the fruit |
| Attitude of the calyx | Spreading | Spreading to reflexed | Spreading to reflexed |
| Size of calyx in relation to fruit diameter | Slightly larger | Slightly larger | Same Size to slightly larger |
| Adherence of calyx | Strong | Strong | Strong |
| Firmness of skin | Strong | Medium | Strong |
| Firmness of flesh | Firm | Medium | Medium |
| Distribution of red color of the flesh | Marginal and central | Marginal and central | Marginal and central |
| Hollow center expression | Weak to moderate | Moderate to strong | Strong |
| Flavor | Very good | Very good | Good to very good |
| Soluble solids (% brix) | 9.5 | 9.2 | 8.7 |
| Time of first flowering | Medium | Early | Early |

TABLE 2-continued

FRUIT CHARACTERISTICS

| Characteristic | 'PRESTIGE' | 'PS-592' (U.S. Plant Pat. No. 9,903) | 'PS-4634' (U.S. Plant Pat. No. 17,487) |
|---|---|---|---|
| Time of first harvesting | Medium | Early | Early |
| Harvest period | Early April to early December | Late March to early December | Late March to early December |
| Type of bearing | Partially everbearing | Partially everbearing | Partially everbearing |

TABLE 3

PLANT CHARACTERISTICS

| Characteristic | 'PRESTIGE' | 'PS-592' (U.S. Plant Pat. No. 9,903) | 'PS-4634' (U.S. Plant Pat. No. 17,487) |
|---|---|---|---|
| Height (cm) | 30.2 | 32.9 | 33.8 |
| Spread (cm) | 36.3 | 37.1 | 37.8 |
| Crowns/plant | 6.5 | 8.0 | 7.3 |
| Size | Medium to large | Large | Large |
| Habit | Globose | Globose | Globose |
| Density | Medium | Medium to open | Medium |
| Vigor | Medium to strong | Strong | Strong |

TABLE 4

STOLON CHARACTERISTICS

| Characteristic | 'PRESTIGE' | 'PS-592' (U.S. Plant Pat. No. 9,903) | 'PS-4634' (U.S. Plant Pat. No. 17,487) |
|---|---|---|---|
| Average number per plant fruiting field | 2.1 | 2.3 | 4.0 |
| Anthocyanin coloration | 7.5R 4/8 to 5/8 | 7.5R 5/6 to 5/4 | 7.5R 4/8 to 5/8 |
| Anthocyanin intensity | Weak to medium | Weak to medium | Weak to medium |
| Diameter at bract (mm) | 3.5 | 4.1 | 3.9 |
| Pubescence | Medium | Medium | Weak to medium |

TABLE 5

FOLIAGE CHARACTERISTICS

| Characteristic | 'PRESTIGE' | 'PS-592' (U.S. Plant Pat. No. 9,903) | 'PS-4634' (U.S. Plant Pat. No. 17,487) |
|---|---|---|---|
| Foliage: | | | |
| Color of upper surface | 7.5GY 4/4 to 3/4 Medium green | 7.5GY 4/4 to 3/4 Medium green | 7.5GY 4/4 to 3/4 Medium green |
| Color of under side | 5GY 5/4 to 6/4 Medium grey green | 5GY 5/4 to 6/4 Medium grey green | 5GY 5/4 to 6/4 Medium grey green |
| Shape in cross section | Slightly convex to strongly convex | Slightly concave | Slightly concave to flat |
| Interveinal blistering | Medium | Medium to strong | Medium to strong |
| Glossiness | Medium | Strong | Medium to strong |
| Number of leaflets | 3 to 4 | 3 | 3 |
| Terminal | | | |

TABLE 5-continued

FOLIAGE CHARACTERISTICS

| Characteristic | 'PRESTIGE' | 'PS-592' (U.S. Plant Pat. No. 9,903) | 'PS-4634' (U.S. Plant Pat. No. 17,487) |
|---|---|---|---|
| Leaflet: | | | |
| Length (cm) | 9.5 | 10.9 | 10.0 |
| Width (cm) | 9.2 | 8.8 | 7.7 |
| Length/width ratio | 1.02 as long as broad | 1.23 much longer than broad | 1.30 much longer than broad |
| Serrations/leaf | 21.6 | 21.3 | 22.8 |
| Size | Medium to large | Large | Medium to large |
| Shape of base | Obtuse | Acute | Acute |
| Shape of teeth | Obtuse | Obtuse | Obtuse |
| Petiole: | | | |
| Length (cm) | 22.7 | 25.1 | 27.3 |
| Diameter (mm) | 4.7 | 5.1 | 4.6 |
| Petiolule length (mm) | 17.4 | 13.2 | 10.0 |
| Pubescence | Moderate | Moderate to sparse | Moderate to sparse |
| Attitude of hairs | Strongly outward | Strongly outward | Slightly outward |
| Stipule: | | | |
| Length (mm) | 19.6 | 21.9 | 19.6 |
| Width (mm) | 8.5 | 9.4 | 9.1 |
| Anthocyanin coloration | Strong | Medium | Strong |
| Color | Light to medium green | Light to medium green | Medium green |

TABLE 6

FRUITING TRUSS CHARACTERISTICS

| Characteristic | 'PRESTIGE' | 'PS-592' (U.S. Plant Pat. No. 9,903) | 'PS-4634' (U.S. Plant Pat. No. 17,487) |
|---|---|---|---|
| Length (cm) | 34.5 | 35.3 | 37.5 |
| Position relative to foliage | Level with | Level with to beneath | Level with |
| Pubescence | Strong | Medium | Medium to weak |
| Anthocyanin intensity | Very light to none | Light | Very light to none |
| Attitude at first pick | Prostrate | Prostrate | Prostrate |

TABLE 7

FLOWER CHARACTERISTICS

| Characteristic | 'PRESTIGE' | 'PS-592' (U.S. Plant Pat. No. 9,903) | 'PS-4634' (U.S. Plant Pat. No. 17,487) |
|---|---|---|---|
| Petal color | N 9.5/90%R to N 9.25/84.2%R White | N 9.5/90%/R to N 9.25/84.2%R White | N 9.5/90%R to N 9.25/84.2%R White |
| Corolla diameter (mm) | 32.2 | 33.0 | 32.7 |
| Calyx diameter (mm) | 34.4 | 36.4 | 36.3 |
| Petal length (mm) | 12.0 | 12.3 | 12.6 |
| Petal width (mm) | 11.5 | 12.1 | 12.5 |

TABLE 7-continued

| FLOWER CHARACTERISTICS | | | |
|---|---|---|---|
| Characteristic | 'PRESTIGE' | 'PS-592' (U.S. Plant Pat. No. 9,903) | 'PS-4634' (U.S. Plant Pat. No. 17,487) |
| Petal length/width ratio | 1.04 | 1.01 | 1.01 |
| Petals/flower | 6.1 | 6.5 | 6.3 |
| Sepal length (mm) | 12.2 | 13.0 | 12.5 |
| Sepal width (mm) | 4.5 | 4.2 | 4.2 |
| Sepal length/width ratio | 2.73 | 3.11 | 2.97 |
| Sepals/flower | 12.3 | 13.1 | 12.9 |
| Size of calyx relative to corolla | Larger | Larger | Larger |
| Size of inner calyx relative to outer calyx | Smaller | Same size to smaller | Same size to larger |
| Relative position of petals | Overlapping | Overlapping | Overlapping |

TABLE 8

| PEST AND DISEASE REACTIONS | | | |
|---|---|---|---|
| Characteristic | 'PRESTIGE' | 'PS-592' (U.S. Plant Pat. No. 9,903) | 'PS-4634' (U.S. Plant Pat. No. 17,487) |
| Two spotted spider mite | Moderately susceptible | Moderately susceptible | Moderately susceptible |
| Flower thrips | Moderately susceptible | Moderately susceptible | Moderately susceptible |
| Powdery mildew | Moderately susceptible | Moderately susceptible | Moderately susceptible |
| Botrytis fruit rot | Moderately susceptible | Moderately susceptible | Moderately susceptible |
| Angular leaf spot | Moderately susceptible | Moderately susceptible | Susceptible |

We claim:

1. A new and distinct strawberry plant named 'PRESTIGE', as herein described and illustrated by the characteristics set forth above.

* * * * *